United States Patent [19]

Matthews et al.

[11] Patent Number: 4,796,617

[45] Date of Patent: Jan. 10, 1989

[54] TRACHEOSTOMY TUBE ASSEMBLY

[76] Inventors: Hugoe R. Matthews, 43 Moor Green Lane, Moseley, Birmingham; Huw B. J. Fischer, Chestons Cottage, Uphampton, Ombersley, Worcestershire, both of England

[21] Appl. No.: 688,484

[22] Filed: Jan. 3, 1985

[30] Foreign Application Priority Data

Jan. 11, 1984 [GB] United Kingdom ............... 8400618

[51] Int. Cl.$^4$ ............................................ A61M 16/00
[52] U.S. Cl. ......................... 128/204.25; 128/205.11; 128/207.15
[58] Field of Search ............... 128/200.26, 204.25, 128/204.21, 207.14, 207.15, 207.16, 205.11, 205.24; 604/118

[56] References Cited

U.S. PATENT DOCUMENTS

| | | | |
|---|---|---|---|
| 2,897,833 | 8/1959 | Seeler | 128/205.11 |
| 3,913,607 | 10/1975 | Price | 128/205.11 |
| 4,409,977 | 10/1983 | Bisera et al. | 128/204.21 |
| 4,488,545 | 12/1984 | Shen | 128/207.14 |
| 4,508,117 | 4/1985 | Rodari | 128/204.25 |
| 4,520,812 | 6/1985 | Freitag et al. | 128/207.14 |

Primary Examiner—Edward M. Coven
Assistant Examiner—K. M. Reichle
Attorney, Agent, or Firm—Pollock, Vande Sande and Priddy

[57] ABSTRACT

A tracheostomy tube assembly has a semi-flexible tube that is coupled at its machine end with an adaptor. The tube is inserted into the patient's trachea through an incision while the adapter is located externally of trachea. The tube has a bore through it that opens into the trachea at its patient end and into the main bore of the adaptor at its machine end. The main bore opens to atmosphere via an aperture in the side of the adaptor. A jet tube is coupled to the adaptor via a narrow bore that is aligned with the main bore. When the jet tube is connected to a high-frequency ventilation source, air is entrained in the adaptor that is directed towards the patient end of the assembly.

2 Claims, 5 Drawing Sheets

TRACHEOSTOMY TUBE ASSEMBLY

BACKGROUND OF THE INVENTION

This invention relates to tracheostomy tube assemblies and ventilation systems.

Ventilation of a patient's lungs may be carried out either by conventional low-frequency ventilation or by high-frequency jet-ventilation. Conventional low-frequency ventilation is carried out usually by means of a cuffed endotracheal tube that has one end inserted within the patient's trachea via his mouth, or by means of a cuffed tracheostomy tube which is inserted via an incision made in the patient s throat. The cuff on the tube is inflated to form a seal between the outer surface of the tube and the wall of the trachea. Gas is supplied along the tube from a ventilating machine to inflate the patient's lungs with a suitable mixture of gases which may include an anaesthetic gas, at a rate of one pulse every several seconds.

High frequency jet-ventilation (such as described in British patent specification GB No. 1 447 987A) makes use of a smaller diameter tube located in the patient's trachea caudally of the vocal chords. Gas is administered by means of short pulses, typically one to ten pulses every second, to produce a jet within the trachea. The action of the jet causes entrainment of gas along the trachea, the combined effect producing ventilation of the patient's lungs. The jet tube can be located via the patient's mouth, nose or through an incision in his throat.

If surgery is being carried out on the upper part of the trachea, it can be a disadvantage to locate the jet tube through the nose or mouth since the tube will provide an obstruction to the surgery. A further disadvantage of previous arrangements is that, because the jet tube opens within the trachea, the expansion of gas as it emerges from the tube causes a cooling effect in the region of the tip of the tube. This can cause damage to adjacent tissue. Locating the tip of the jet tube within the trachea causes entrainment of gas within the trachea which will be a mixture of expiratory gas and fresh gas, thereby having a reduced oxygen content. Such arrangements also make it more difficult to analyze gas flows and monitor the quality of gas administered to the patient.

BRIEF SUMMARY OF THE INVENTION

It is an object of the present invention to provide a tracheostomy tube by which such previous disadvantages and difficulties can be alleviated.

According to one aspect of the present invention there is provided a tracheostomy tube assembly comprising a first tubular portion inserted in the trachea through an incision in the throat, and a second tubular portion located externally of the trachea, the second tubular portion having a bore therein in communication with a bore through the first tubular portion, the bore in the second tubular portion being open to atmosphere via an aperture, the assembly including a jet tube that is open to the bore in the second tubular portion via an opening having a cross-sectional area less than that of the bore, and the opening and the tube being arranged to provide a high-frequency jet-ventilation outlet into the bore which entrains air via the aperture and directs it towards the patient end of the assembly.

Because the jet ventilation outlet is external of the trachea the majority of the cooling effect of the expanding gas occurs outside the trachea, thereby reducing damage to the patient's trachea. As the bore in the second tubular portion is open to the atmosphere, air will be entrained into the trachea by the jetting effect of gases supplied to the jet tube. This provides a higher oxygen content than is possible with entrainment of gas in the upper trachea and also facilitates the monitoring of the quality of gas administered.

The bore in the second tubular portion may open to atmosphere between the ends of the assembly. The assembly may include a rotatable sleeve for closing the aperture. The bore and opening are preferably aligned in the second tubular portion, and the bore may be enlarged at its machine end in the region of the aperture. The second tubular portion is preferably formed separately of the first tubular portion and is removable therefrom. The first tubular portion preferably has an external diameter substantially smaller than the internal diameter of the patient's trachea, and may be flexible but sufficiently rigid to prevent substantial deflection of the patient end by ventilation gas pulses.

According to another aspect of the present invention there is provided a ventilation system comprising a tracheostomy tube assembly having a first tubular portion inserted in the trachea through an incision in the throat, and a second tubular portion located externally of the trachea, the second tubular portion having a bore therein in communication with a bore through the first tubular portion, the system also comprising a high-frequency ventilation unit coupled with the assembly to produce high-frequency gas ventilation, the bore in the second tubular portion being open to atmosphere via an aperture, the assembly including a jet tube that is open at one end to the bore in the second tubular portion via an opening having a cross-sectional area less than that of the bore, and the jet tube being coupled at its other end to the ventilation unit so that high frequency jet-ventilation gas pulses are directed to the patient end of the assembly.

A ventilation system and a tracheostomy tube assembly, both in accordance with the present invention, will now be described, by way of example, with reference to the accompanying drawings.

DETAILED DESCRIPTION

Figure 1:
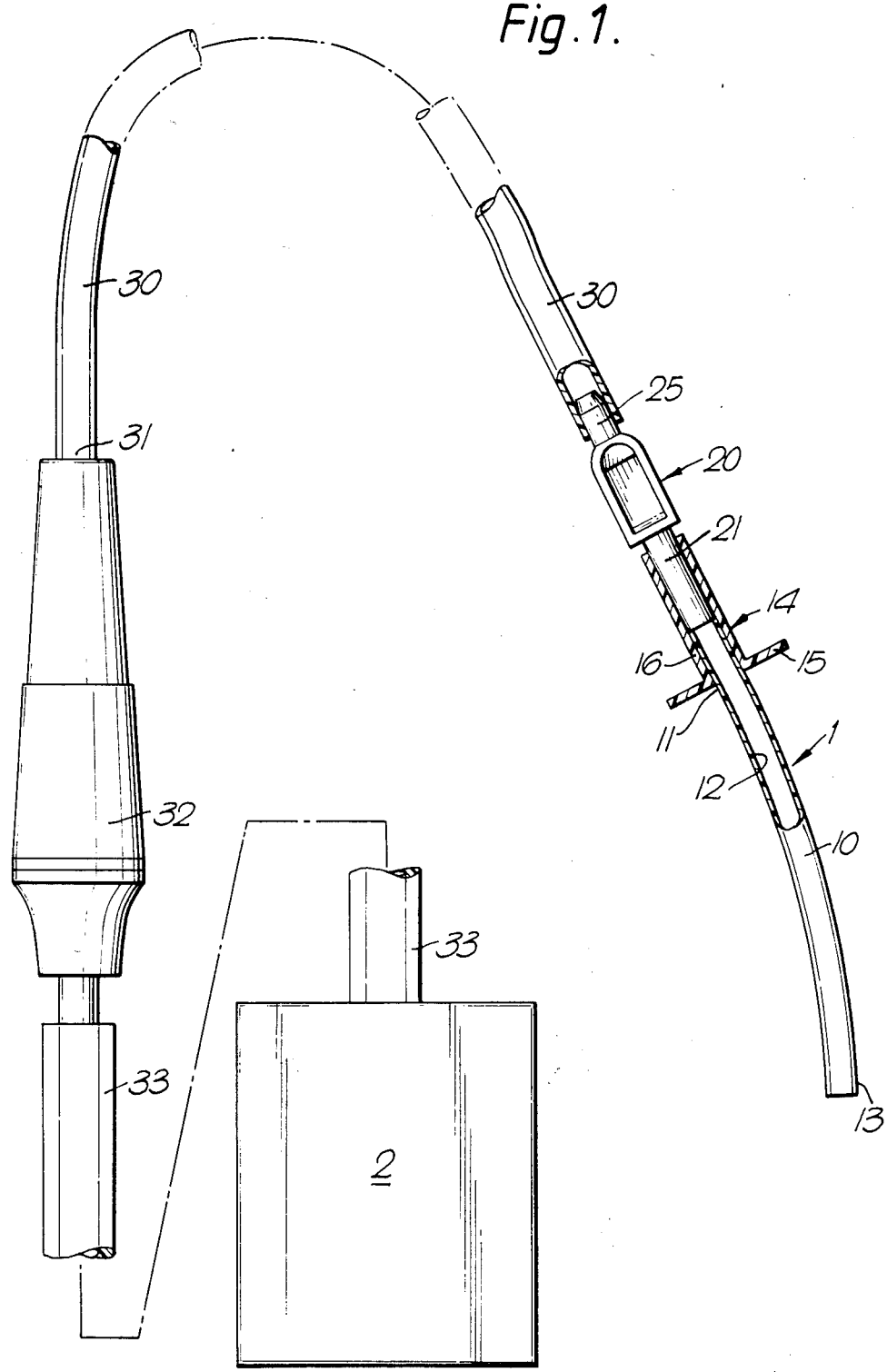
FIG. 1 is a partly sectional view of the system.

With reference to FIG. 1, the system comprises a tracheostomy tube assembly 1 and a high frequency ventilation unit 2 coupled to the assembly.

The tracheostomy tube assembly 1 is made up of a main tube 10 to the rear or machine end 11 of which is secured in an adaptor 20. The tube 10 is of a translucent PVC having an internal bore 12 with a diameter of 4 mm. The external diameter of the tube 10 is 5.4 mm which is substantially less than the internal diameter of the trachea. The nature of the material forming the tube 10 and its dimensions are chosen such that the tube is flexible but maintains sufficient rigidity that the patient end 13 of the tube will not be deflected substantially by gas pulses from the ventilation unit 2. This ensures that the lining of the trachea is not damaged by any whiplashing effect at the patient end of the tube. The tube 10 is curved in an arc of radius about 180 mm and projects 80 mm from a flange assembly 14 secured to the machine end of the tube. The flange assembly 14 is of a soft flexible plastics and comprises a rectangular flange 15 that extends radially of the tube 10, and an integral sleeve 16 that projects 18 mm to the rear of the flange. The tube 10 is secured in the patient end of the sleeve 16 by means of a solvent, adhesive or by welding.

Figure 2:
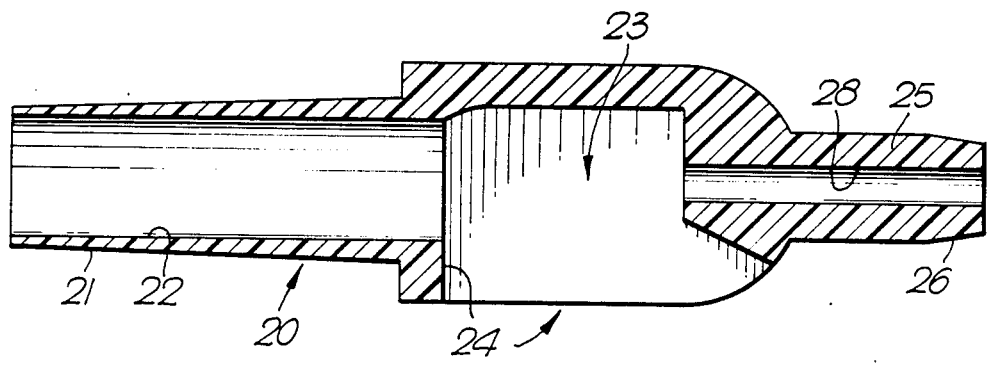
FIG. 2 is a cross-sectional side elevation of a part of the assembly.
Figure 3:
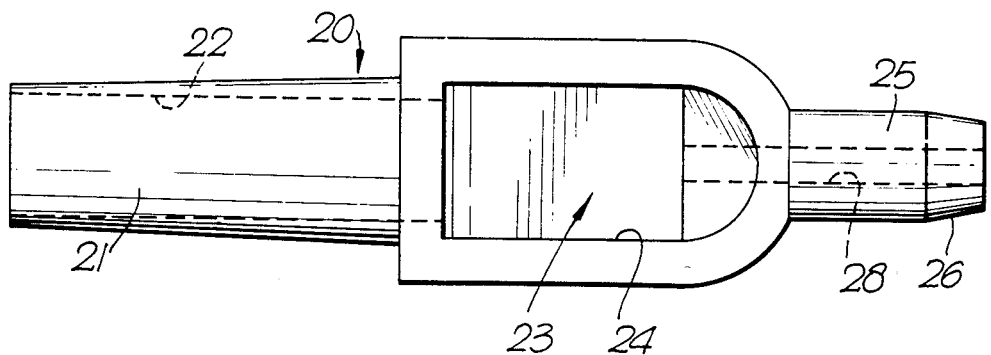
FIG. 3 is a view from below of that part of the assembly shown in FIG. 2.

With reference now also to FIGS. 2 and 3, the adaptor 20 is in the form of a tubular rigid plastics moulding about 32 mm in length. The adaptor 20 is a push fit at its patient end 21 in the machine end of the sleeve 16 of the flange assembly 14. The patient end 21 of the adaptor is tapered on its external surface and has a bore 22 of 4 mm diameter which is the same size as that of the bore 12 through the tube 10. When inserted in the sleeve 16, the patient end 21 of the adaptor 20 abuts the machine end 11 of the tube 10 so that a smooth internal surface for gas flow is produced.

At a location between the ends of the adaptor 20, the bore 22 is enlarged to form a venturi chamber 23 of increased cross-sectional area which is open to the atmosphere through an aperture 24 having an area between about 25 to 30 mm$^2$. A spigot 25 with a tapered tip 26 extends from the machine end of the adaptor. The spigot 25 has an axial bore 28 with a diameter of 1.4 mm, giving it a smaller cross-sectional area than the bore 22 through the patient end of the adaptor. The bore 28 also opens into the chamber 23 at its patient end and is axially aligned with the bore 22 at the patient end of the adaptor.

The spigot 25 has sealed with it, the forward end of a high-frequency jet-ventilation tube 30. The tube 30 has an outside diameter between about 2.7 mm and 3.3 mm, and an internal diameter between about 1.7 mm and 2.3 mm. The tube 30 is of a flexible, plastics material and is typically about 250 mm long, being terminated at its rear end 31 with a female luer-lock connector 32. The connector 32 may be closed by a suitable cap when not required but is, in use, coupled to a length of semi-rigid tubing 33 that extends to the high-frequency jet-ventilation unit 2. The jet tube 30 opens into the chamber 23 of the adaptor 20 via the bore 28 which forms a restricted opening having a cross-sectional area smaller than that of the chamber 23 and of the bore 22. In alternative arrangements the bore through the jet tube 30 could open into the chamber 23 directly, the bore of the jet tube itself providing an opening of restricted size compared with that of the chamber 23 and the bore 22.

The assembly need not have a separately formed adaptor, in the manner described above. Instead, the assembly could be an integral unit, the jet tube opening into that portion of the assembly located externally of the trachea. However, by having a removable adaptor in the manner referred to above, there is the advantage that the adaptor can be removed to leave the tube in place when high frequency ventilation is not required.

Figure 4:
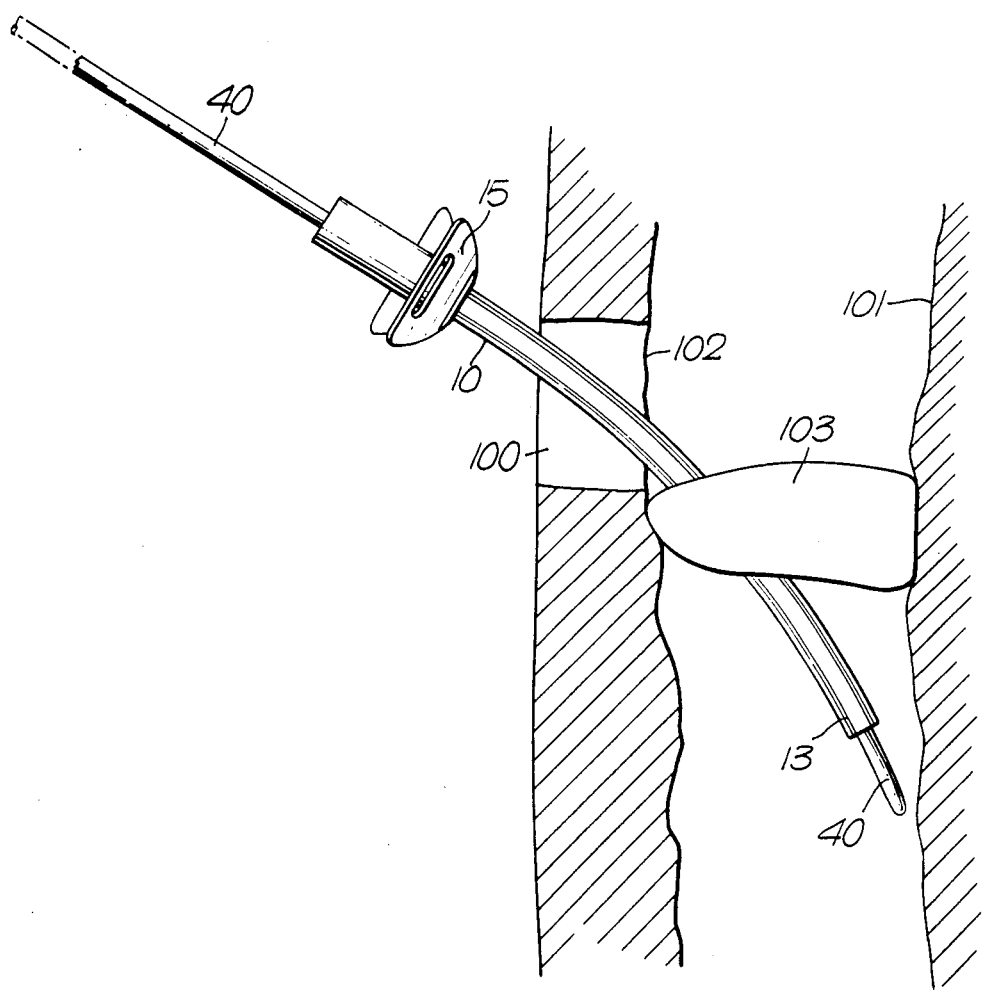
FIGS. 4 and 5 illustrate the assembly and system in use.
Figure 5:
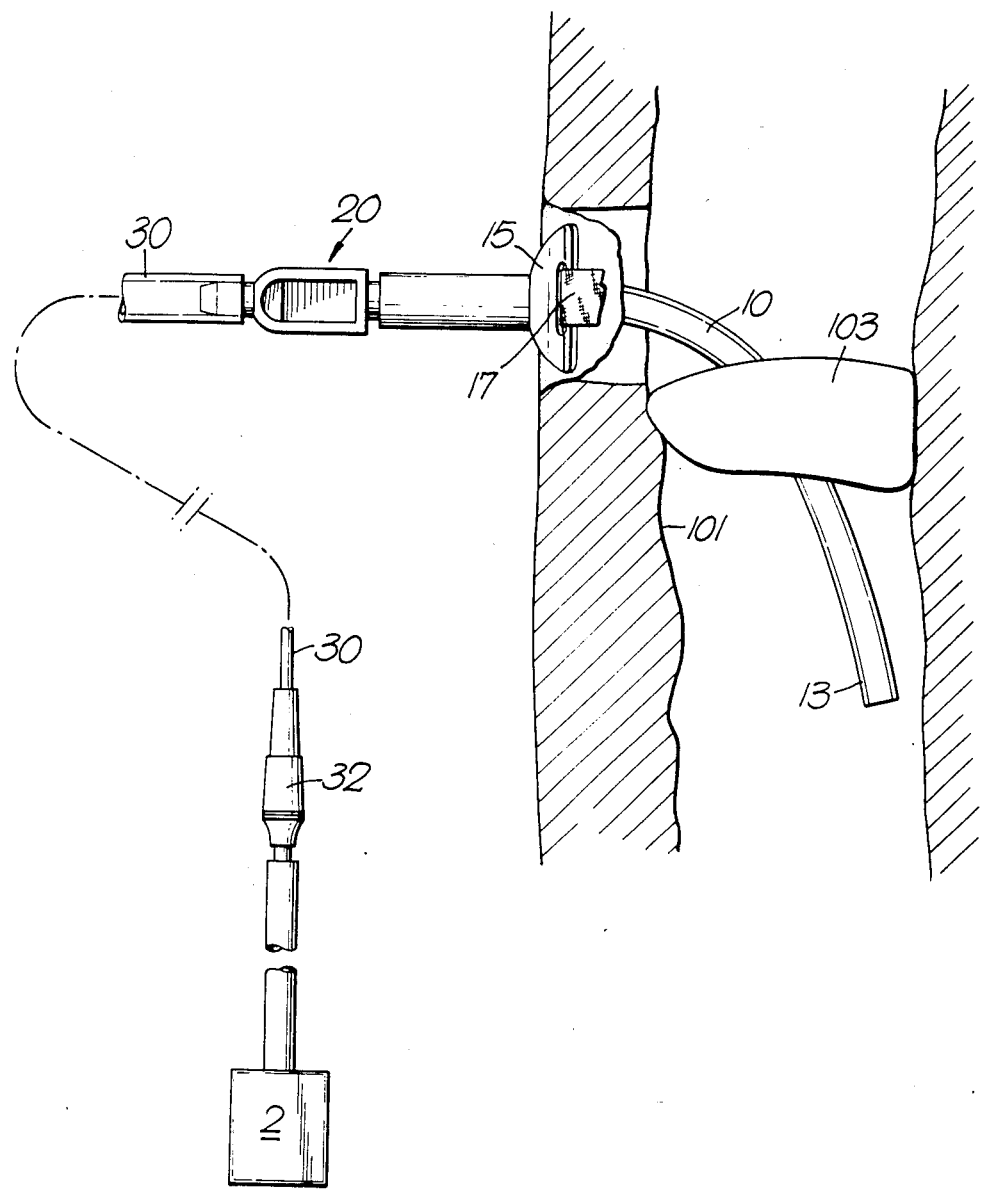

The system is used in the manner shown in FIGS. 4 and 5. First, as shown in FIG. 4, a small cut 100 is made into the trachea 101 with a scalpel through the cricothyroid membrane 102 which lies above the cricoid cartilage 103; this cut can be a vertical slit about 10 mm long. A stylet 40, having the same curvature as the tube 10, is inserted through the cut 100 into the trachea. The tube 10 is then slid over the stylet so that the patient end 13 of the tube is inserted caudally into the trachea until the flange 15 contacts the neck of the patient. The stylet 40 is then removed leaving the tube 10 in place. The length of the tube 10 is such that the patient end 13 of the tube is close to the patient's carina (not shown) but does not reach it, since this could result in inflation of only one lung. In this respect, the maximum length of the tube 10 is about 100 mm from the flange.

After insertion of the tube 10, the adaptor 20, with the jet tube 30 in place, is pushed onto the machine end of the sleeve 16, as shown in FIG. 5, so as to couple the assembly to the ventilation unit 2. The assembly is secured in position by means of a tape 17 passed through slots in the flange 15 and fastened to or about the patient's neck. Operation of the ventilation unit 2 causes supply of humidified gas pulses at a frequency of typically 60–300 pulses a minute. These pulses produce a jet at the forward end of the jet ventilation tube 30 which is directed towards the patient end of the assembly. The jet effect causes entrainment of air from the chamber 23 of the adaptor 20 drawing in atmospheric air through the aperture 24 and delivering this to the patient end 13 of the tube 10, thereby ventilating the patient's lungs. Because the major part of the drop in pressure of the ventilation supply occurs within the adaptor 20, that is, outside the trachea, the cooling effect that this produces is confined externally and does not cause damage to the trachea lining. The oxygen content of air supplied to the lungs is higher than when gas entrainment occurs within the trachea because atmospheric air is entrained rather than a mixture of atmospheric and exhaled gas. Because atmospheric air is entrained, this also makes it easier to analyze accurately gas flows and gas exchange than when air is entrained from within the trachea, since the composition of air within the trachea is not accurately known.

It is also possible to use the assembly in an alternative ventilation mode. In such an arrangement the assembly includes means (not shown) for closing the aperture 24 which may, for example, take the form of a rotatable sleeve that embraces the adaptor. The sleeve would be provided with an opening which, in normal use is aligned with the aperture 24 but which, in the alternative mode, is displaced so that the sleeve closes the aperture 24. In the alternative ventilation mode, the high-frequency ventilation gas pulses cause entrainment of gas at the patient end of the assembly, within the trachea. Because there is still a pressure drop within the adaptor, in this alternative mode, the major part of the cooling effect is confined externally of the trachea. This alternative mode may be more suitable when higher pressures are required to ventilate the lungs.

The assembly may be used to introduce a suction catheter (not shown) into the trachea and bronchial tract. The catheter can be inserted through the aperture 24 in the adaptor 20, along the bore 22 in the adaptor and the bore 12 in the tube 10. In this way, tracheobronchial secretions can be periodically removed, as necessary, without the need to disconnect the adaptor. Introduction of a suction catheter is facilitated because entry to the trachea is made through the cricothyroid membrane. The action of high-frequency ventilation causes vibration of the lungs, thereby loosening sputum and facilitating its removal with a suction catheter.

Figure 6:
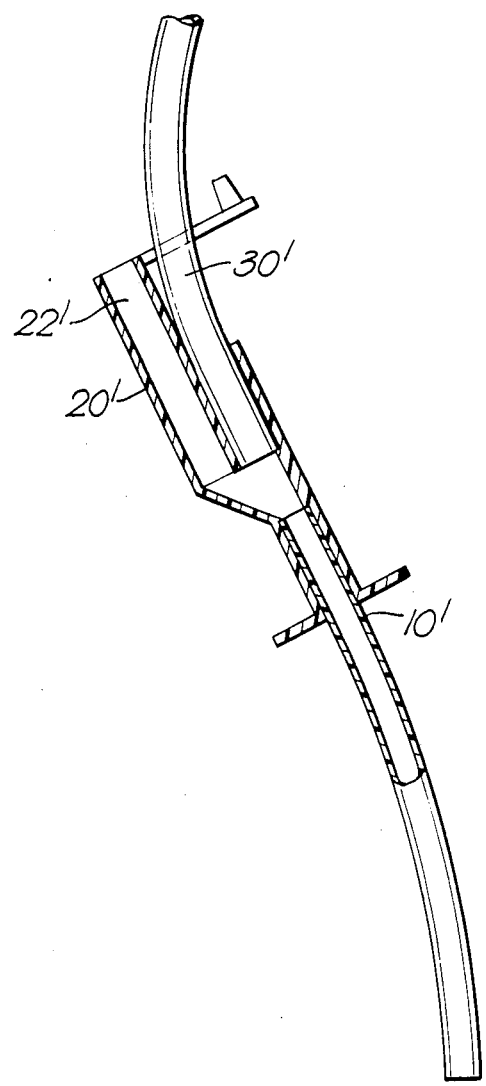
FIG. 6 is a partly sectional view of an alternative form of assembly.

The assembly could take various different forms, one of which is shown in FIG. 6. In this form the assembly has an adaptor 20' that is mounted at the rear end of a tube 10', in a similar manner to that described above. In the alternative form, however, the jet tube 30' opens into the adaptor 20' at a location between its ends, the adaptor having a bore 22' that opens to atmosphere at the patient end of the assembly, the bore 22' being selectively blockable by means of a plug (shown in FIG. 6) which is attached by a flexible arm to adaptor 20' adjacent the open end of bore 22'.

The assembly of the present invention has the advantage of producing high gas exchange in the patient's lungs with low intra thoracic pressures which is useful for patients with cardiac problems. The high-frequency ventilation produces little movement of the lungs and is therefore also useful for lung surgery. Because the tube is of small diameter compared with the patient's trachea and because the tube is not sealed with the trachea by means of a cuff or other device, the patient is able to speak, eat, drink and cough normally. As the patient's respiratory system starts to recover they become partially capable of satisfying respiratory demands while the high-frequency ventilation is taking place. In conventional forced ventilation the patient is not able to exercise his own respiratory muscles in this way thereby delaying recovery. The assembly can be tolerated by patients without the need for sedation, as needed when using conventional endotracheal tubes. This also improves the patient's morale and makes recovery quicker.

What we claim is:

1. A tracheostomy tube assembly comprising a main tube having a patient end and a machine end, the patient end of the main tube being inserted into the trachea of a patient through an incision in the patient's throat, the patient end of said main tube being configured such that gas flow along the trachea around the main tube is substantially unimpeded, and a substantially tubular adaptor that is joined to the machine end of the main tube close to and external of the throat of the patient, the adaptor including: means defining a cavity; a first bore extending from said cavity to said main tube; a high frequency jet tube, one end of said jet tube opening into said cavity and being directed towards said first bore, the cross-sectional area of said jet tube being less than that of said cavity; an aperture that opens into said cavity; and means for selectively completely blocking said aperture; said aperture opening to atmosphere when unblocked such that high-frequency jet-ventilation pulses supplied to said jet tube cause entrainment of air from the aperture towards the patient end of the main tube, the cross-sectional area of the patient end of the main tube being small enough that when said aperture is completely blocked by said blocking means the said high-frequency jet-ventilation pulses are produced at the patient end of the main tube and are operative to entrain gas within the trachea.

2. A ventilation system comprising a tracheostomy tube assembly having a first tubular portion inserted in the trachea of a patient through an incision in the patient's throat, the first tubular portion being configured such that gas can flow along the trachea around the first tubular portion substantially unimpeded, and a second tubular portion located externally of the trachea, the second tubular portion having a bore therein in communication with a bore through the first tubular portion, the system also comprising a high-frequency ventilation unit coupled with the assembly to produce high-frequency gas ventilation, the second tubular portion having a selectively blockable aperture therein, means for selectively completely blocking said aperture, the bore in the second tubular portion opening to atmosphere via said aperture when said aperture is unblocked, the assembly including a jet tube and an opening through which said jet tube opens to the said bore in the second tubular portion, said jet tube and said opening being disposed such that gas flowing through said jet tube is directed towards said first tubular portion, the area of said opening transverse to the direction of flow through the opening being less than that of the said bore in the second tubular portion, the jet tube being coupled at its other end to the ventilation unit so that high-frequency jet-ventilation gas pulses cause entrainment of air via said aperture within said assembly when the said aperture is unblocked, and the cross-sectional area of the patient end of the first tubular portion being small enough to cause entrainment of air in the trachea when said aperture is completely blocked by said blocking means.

* * * * *